US006738136B2

(12) United States Patent
Norton et al.

(10) Patent No.: US 6,738,136 B2
(45) Date of Patent: May 18, 2004

(54) ACCURATE SMALL-SPOT SPECTROMETRY INSTRUMENT

(75) Inventors: Adam Norton, Palo Alto, CA (US); Abdurrahman Sezginer, Los Gatos, CA (US); Fred E. Stanke, Cupertino, CA (US); Rodney Smedt, Los Gatos, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/290,730

(22) Filed: Nov. 7, 2002

(65) Prior Publication Data

US 2003/0090655 A1 May 15, 2003

Related U.S. Application Data

(60) Provisional application No. 60/337,678, filed on Nov. 9, 2001.

(51) Int. Cl.[7] .............................. G01J 3/08; G01J 3/42

(52) U.S. Cl. ....................................... 356/326; 356/446

(58) Field of Search ................................ 356/326, 328, 356/445, 446, 447, 448

(56) References Cited

U.S. PATENT DOCUMENTS

| | | | | |
|---|---|---|---|---|
| 4,776,695 A | | 10/1988 | van Pham et al. | 356/328 |
| 5,659,397 A | * | 8/1997 | Miller et al. | 356/446 |
| 5,747,813 A | | 5/1998 | Norton et al. | 250/372 |
| 2002/0021441 A1 | | 2/2002 | Norton et al. | 356/326 |

FOREIGN PATENT DOCUMENTS

| | | | |
|---|---|---|---|
| JP | 57-106846 | 7/1982 | G01N/21/62 |
| WO | WO 00/57127 | 9/2000 | G01B/11/06 |

OTHER PUBLICATIONS

K. Goto et al., "On–line System for Measuring Thickness of Hydrated Chromium Oxide Film on Tin Free Steel," *Iron and Steel*, Issue 9, 1984, pp. 1088–1094. (includes translation).

G. Harbeke et al., "Rapid Characterization of Polysilicon Films by Means of a UV Reflectometer," *RCA Review*, vol. 44, Mar. 1983, pp. 19–29.

* cited by examiner

*Primary Examiner*—F. L. Evans
(74) *Attorney, Agent, or Firm*—Stallman & Pollock LLP

(57) ABSTRACT

The invention is a method and apparatus for determining characteristics of a sample. The system and method provide for detecting a monitor beam reflected off a mirror, where the monitor beam corresponds to the intensity of light incident upon the sample. The system and method also provide for detecting a measurement beam, where the measurement beam has been reflected off the sample being characterized. Both the monitor beam and the measurement beam are transmitted through the same transmission path, and detected by the same detector. Thus, potential sources of variations between the monitor beam and the measurement beam which are not due to the characteristics of the sample are minimized. Reflectivity information for the sample can be determined by comparing data corresponding to the measurement beam relative to data corresponding the monitor beam.

12 Claims, 5 Drawing Sheets

Figure 1, Prior Art

ACCURATE SMALL-SPOT SPECTROMETRY INSTRUMENT

RELATED APPLICATION

The present application claims the benefit of U.S. Provisional Application Serial No. 60/337,678, filed Nov. 9, 2061, titled ACCURATE SMALL-SPOT SPECTROMETRY INSTRUMENT which is incorporated herein by reference in its entirety.

FIELD OF THE INVENTION

The present invention relates generally to metrology instruments, and more particularly to spectrometry instruments that measure the reflectivity of a sample.

BACKGROUND

In semiconductor manufacturing and other fields it is desirable to make quantitative measurements of a sample's reflectivity properties over very small, selectable areas and over as broad a band of wavelengths as possible. Instruments for making these measurements typically incorporate microscope-like objective lenses for focusing light on the sample. One type of illumination source is a Xenon arc lamp. In order to scan to various positions on the sample of interest a portion of the optics can be moved with respect to a stationary portion of the optics, or the sample can be moved with respect to at least some portion of the optics, or both.

A common issue with such instruments is guaranteeing the stability of the light which is incident upon the sample, or at least knowing the spectral intensity of the incident light, so that the detected light reflected from the sample can be evaluated relative to the intensity of the light incident on the sample. Since reflectivity is defined as the ratio of the intensity of light reflected off the sample relative to the intensity of light incident upon the sample, accurate reflectivity measurements depend knowing the incident light intensity.

There are several factors that can make it difficult to determine the intensity of the light upon the sample. One factor is that the characteristics of most sources of light change with time, and thus the intensity of the incident light can vary with time. Another factor is that where there is relative motion of the illumination source and the rest of the optics, either via (nearly) collimated light paths or optical fibers, there can be changes in the transmission efficiency of illuminating light as a function the scan position, or scan state. Here scan state includes the history of previous scan positions. This is important, for example, with some architectures using a fiber to transmit light from the light source. One prior system is shown in US Patent Application, publication number US 2002/0021441 A1 (SMALL SPOT SPECTROMETRY INSTRUMENT WITH REDUCED POLARIZATION) and in PCT application, international publication number WO 00/57127 (METHOD AND APPARATUS FOR WAFER METROLOGY); both of these references are incorporated herein by reference in their entirety.

FIG. 1 shows another type of prior system 100. The system 100 includes a light source 102 and a transmission means 104 for light generated by the light source 102 The light transmitted through the transmission means 104 is then transmitted through a collimating, lens 108, and leaves the collimating lens as light beam 106. The light beam is then incident upon a beam splitter 110. A first beam 140 is transmitted from the beam splitter through a lens 144 and then through a plate 146 having pinhole to receive the first beam 140. The first beam 140 is then transmitted through a transmission means 148 and received by a detector 150. In response to the light received, the detector 150 generates a monitor signal corresponding to the received light. This monitor signal from the detector 150 is received by a processor 160 which analyzes the monitor signal and uses it relative to a signal generated by detector 130.

In addition to the beam 140 being transmitted through the beam splitter 110, beam 112 is also reflected from the beam splitter 110 through an objective lens 114 and onto a spot 118 on a sample 116 being analyzed. Some portion 113 of the light 112 is reflected off the sample and back through the objective lens 114. This light 113 is further transmitted through the beam splitter 110 and off a turn mirror 122 and through a lens 124. The resulting light beam is then transmitted through a pinhole in a plate 126 and into a transmission means 128. The light transmitted through the transmission means 128 is received by the detector 130. In response to receiving this light the detector 130 generates a sample signal which corresponds to the received light. This sample signal is received by the processor 160 where it is analyzed relative to the monitor signal received from the detector 150.

The fact that prior systems provide for transmitting a monitor beam 140 and a measurement beam 113 through different transmission paths and provide for using different detectors (150 and 130) for detecting the monitor light beam and the measurement light beam introduces a number of potential sources which could generate variations in the monitor signal relative to the measurement signal which are not related to the reflective properties of the sample. What is needed is a system which reduces possible sources of extrinsic variations in the monitor beam relative to the measurement beam.

SUMMARY OF THE INVENTION

One embodiment herein provides a system for measuring characteristics of a sample. This system includes a light source for generating a beam of light which is directed toward a sample, and a mirror which can be moved between a first position and a second position, wherein in the first position the mirror is positioned between the light source and the sample such that light generated by the light source is reflected off the mirror and transmitted through a first path. The first path consists of a reflection path. In the second position the mirror is positioned such that it is not between the light source and the sample, and light generated by the light source is reflected off the sample and transmitted through the reflection path. This system also provides a detector coupled to the reflection path which generates a monitor signal in response to receiving light reflected from the mirror, and generates a measurement signal in response to light reflected from the sample.

Another embodiment includes a method for determining characteristics of a sample in a system having a light source, and a movable mirror. The method includes generating a light beam and directing the light beam toward the sample, and positioning the movable mirror such that it is in a first position, where it reflects the light beam along a first path, wherein the first path consists of a reflection path. The method also includes generating a monitor signal which corresponds to the light reflected from the mirror, and positioning the movable mirror such that it is in a second position, where it does not reflect the light beam which is directed toward the sample, wherein the light beam which is directed toward the sample is reflected off the sample along the reflection path. The method of this embodiment also includes generating a measurement signal which corresponds to the light reflected from the sample, and analyzing the measurement signal relative to the monitor signal to determine properties of the sample.

Another embodiment includes a system for measuring characteristics of samples. The system includes a light source for generating a beam of light, and beam splitter for directing the beam of light toward a sample. The system also includes a lens disposed between the beam splitter and the sample for focusing the beam of light on the sample, such that a measurement beam of light is reflected off the sample, wherein after the measurement beam is reflected off the sample, it is transmitted through a reflection path. The system includes a detector positioned to receive light transmitted through the reflection path wherein in response to receiving light transmitted through the reflection path the detector generates a signal corresponding to the light transmitted through the reflection path, and a mirror which can be moved between a first position and a second position, wherein in the first position the mirror is positioned between the beam splitter and the sample, such that light directed by the beam splitter toward the sample is incident upon the mirror and reflected through a first path, wherein the first path consists of the reflection path, wherein in the second position the mirror is positioned such that light directed by the beam splitter toward the sample is reflected off the sample along the reflection path. The system further includes a processor coupled to the detector which uses a first signal generated by the detector in response to receiving light reflected from the mirror and a second signal generated by the detector in response to light reflected from the sample, to determine characteristics of the sample.

DESCRIPTION OF THE PREFERRED EMBODIMENTS

Figure 2:
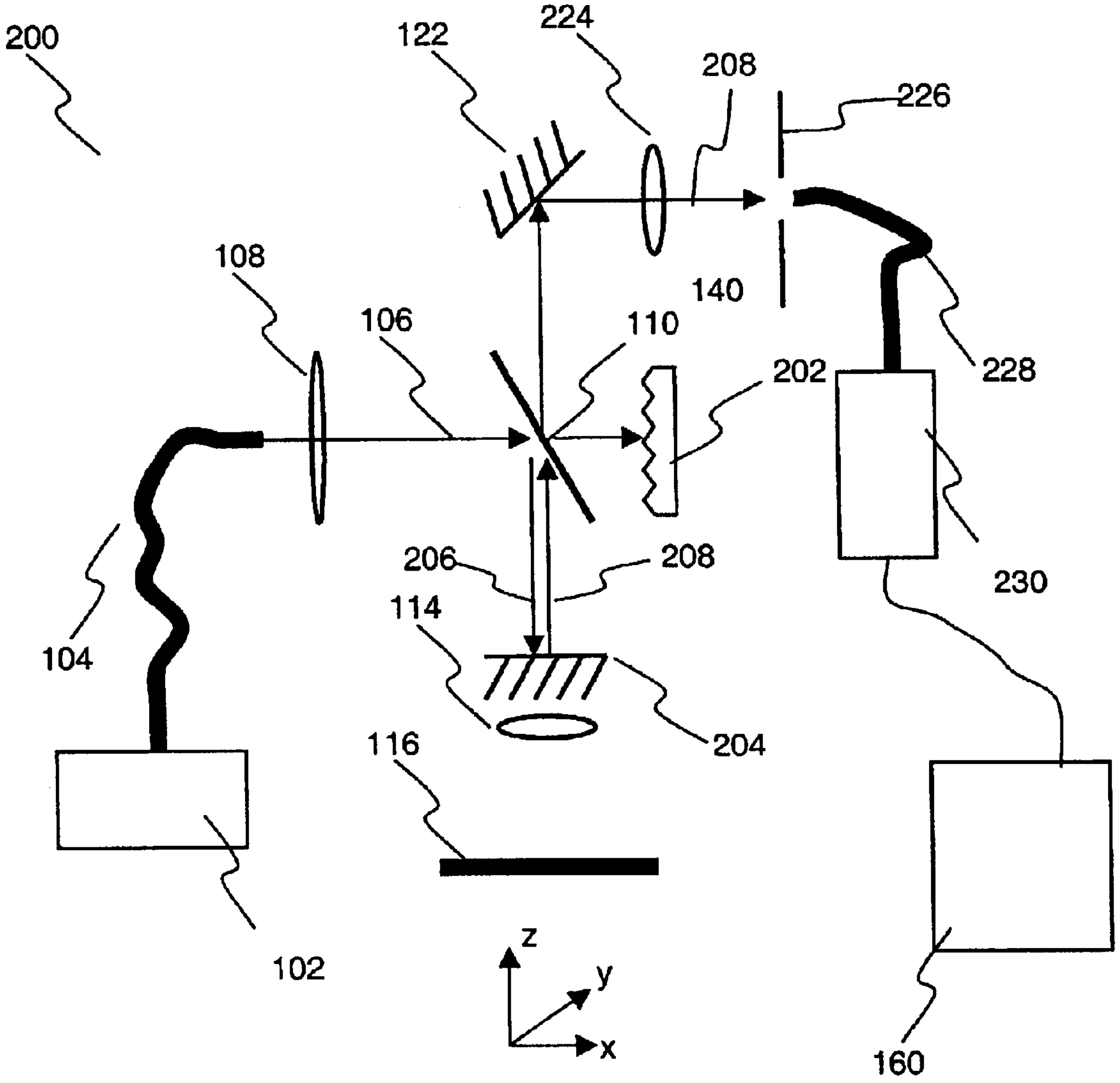
FIG. 2 is a schematic view of an embodiment of the present invention in a first state.

FIG. 2 illustrates one embodiment of a multiplexed spectrometer system 200 of the present invention in a first state. The system 200 includes a light source 102 coupled to a transmission means 104, such as an optic fiber. The light transmitted through the transmission means 104 is then transmitted through a collimating lens 108 which transmits a beam of light 106. The beam of light 106 is then incident upon a beam splitter 110. An absorber 202 absorbs light passing through beam splitter 110. Illumination beam 206 reflects from the beam splitter 110 toward a sample 116. A movable mirror 204 is shown in a monitor position. In the first position, the mirror 204 is positioned between the beam splitter 110 and the sample 116, such that it reflects beam 208 through a reflection path. As part of this reflection path, the reflected beam 208 passes through the beam splitter 110, reflects off an optional turn mirror 122, and passes through focusing optics 224, such as a lens, onto a pinhole in a plate 226. Reflected beam 208 then passes through a transmission means 228, such as an optic fiber and is then received by a detector 230. Typically, the detector 230 will be a spectrometer, which detects the intensity of different wavelengths of light. One type of spectrometer includes an optical element for angularly dispersing a light beam as a function of wavelength. This dispersed light is then measured by an array of detector elements. With system 200 in the first state, detector 230 generates a monitor signal corresponding to the intensities at different wavelengths of light reflected from movable mirror 204, and not from sample 116. The processor 160 then uses the monitor signal as an indication of intensity in the illuminating light, based on the assumption that mirror 204 does not change with time, i.e., between calibrations, as discussed below.

Figure 3:
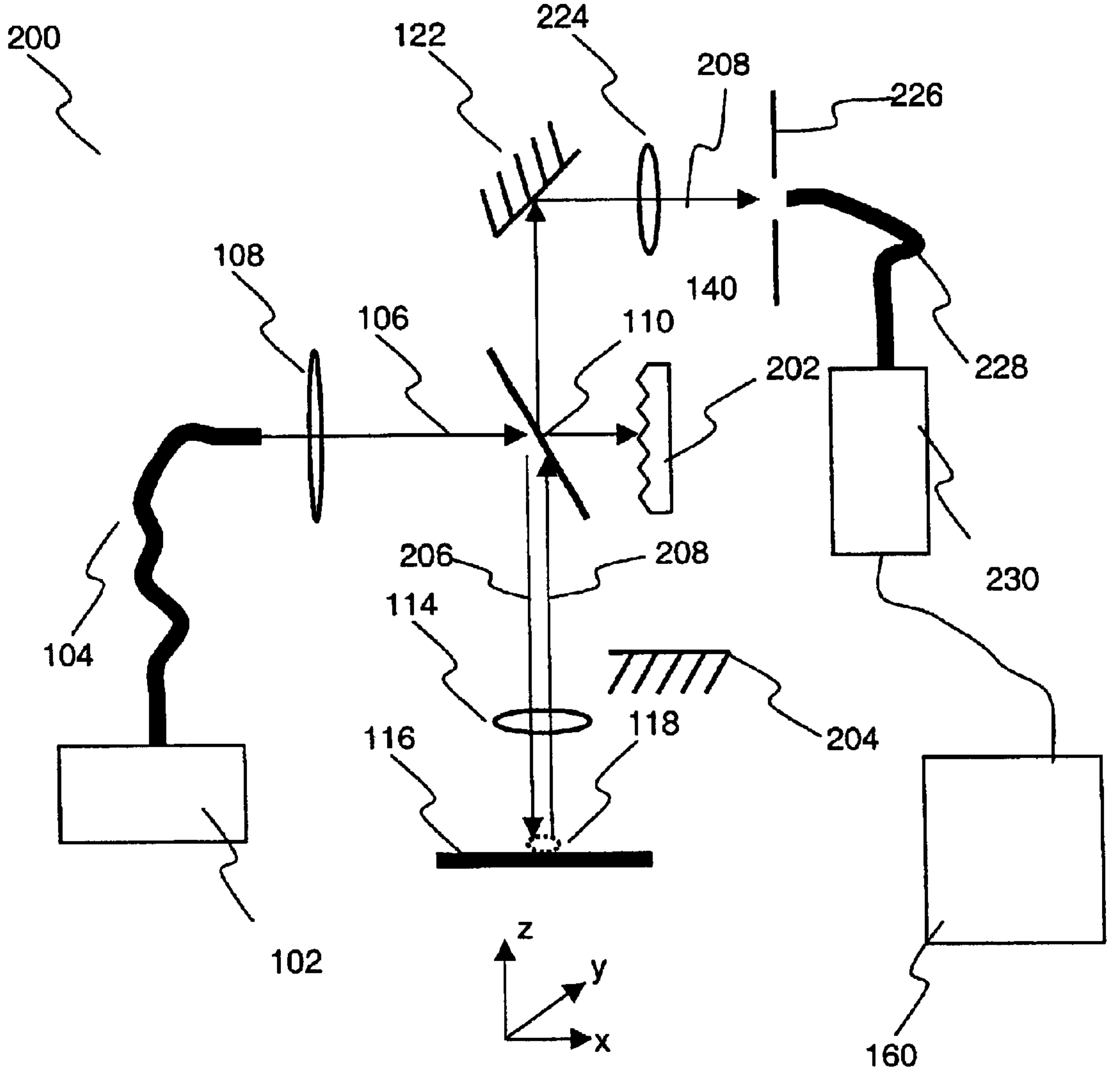
FIG. 3 is a schematic view of an embodiment of the present invention in a second state.

FIG. 3 shows the system 200 in a second state where the movable mirror 204 is in second position. As shown in the second position, the mirror 204 is not between the beam splitter 110 and the sample 116. As in FIG. 2, the light beam 106 is incident upon the beam splitter 110, and the absorber 202 absorbs light passing through the beam splitter 110. Again illumination beam 206 reflects from beam splitter toward the sample 116. In this second state, beam 206 passes through an objective lens 114 and is incident upon at least a small spot 118 on the sample 116. Reflected beam 208 is then transmitted through the reflection path, as described above, and received by detector 230. The detector 230 then generates a sample signal indicative of the reflectance of spot 118.

Apparatus 200 is generally for measuring the reflectivity of a sample. Reflectance is defined as the ratio of intensities incident upon and reflected from the sample. System 200 must be calibrated in order to measure reflectance. Calibration finds the relationship between measured signals and samples with known calibration reflectivities. Calibration may include the steps of estimating the calibration reflectivities. Calibration preferably allows for changes to system 200 over relatively long time scales, e.g., months. In the discussion that follows, all signals from spectrometer 230 are preferably dark corrected by subtracting signals collected with no light, e.g., from transmission means 104, as is known in the art. Further, the signals may alternatively be additionally corrected for scattering of light within spectrometer 230, as is also known in the art. A sample signal is collected with mirror 204 retracted so that sample 116 reflects reflected beam 208, as in FIG. 3, and a monitor signal collected with mirror 204 reflecting reflected beam 208, as shown in FIG. 2.

In an embodiment of system 200, and in another embodiment as described in PCT application no. PCT/US00/07709 entitled APPARATUS FOR WAFER METROLOGY (which is hereby incorporated by reference in its entirety) the system 200, at any desired time when system is in use, locate spot 118 on a reference sample whose reflectivity does not change with time, and collect a reference measurement signal. The reference measurement signal has a corresponding reference monitor signal. In some embodiments, the reference measurement and monitor signals are collected at a time as close as practical to the time for collecting the sample measurement and monitor, e.g., with a time difference of less than a minute.

The estimated value of the reflectance is given by $$R(\lambda,r)\sim=S(\mathbf{1},\lambda,r)S(\mathbf{2},\lambda,r_0)/[F\mathbf{1}(\lambda,r)S(\mathbf{2},\lambda,r)S(\mathbf{1},\lambda,r_0)]-F\mathbf{0}(\lambda,r)/F\mathbf{1}(\lambda,r) \quad \text{Eq 1}$$

where S(1, λ,r) is the measurement signal from the sample at location r when mirror 204 is in its second state, S(2, λ, r) is the corresponding monitor signal at the same location (e.g. with the optics in the same position as when the measurement signal for location r is generated) when mirror 204 is in its first state. S(1, λ, $r_0$) is the measurement signal from the reference reflector at $r_0$ acquired at a proximate time, S(2, λ, $r_0$) is the corresponding reference monitor signal, F0(λ,r) and F1(λ,r) are first and second calibration functions, λ is wavelength, r specifies the position of spot 118 relative to sample 116, and $r_0$ is the relative position of the reference sample. The calibration functions are the result of minimizing $$\sum_{n=1}^{N}\left(\frac{S(n,1,\lambda,r)S(n,2,\lambda,r_0)}{S(n,2,\lambda,r)S(n,1,\lambda,r_0)} - F0(\lambda,r) - F1(\lambda,r)R_c(n,\lambda,r)\right)^2 \quad \text{Eq 2}$$

with respect to F0(λ,r) and F1(λ,r). $R_c$(n,λ,r) are reflectance of calibration samples. The signals S and reflectances $R_c$ have an additional integer index n=1,2, . . . ,N that labels the calibration samples. N is the number of calibration samples. In the preferred implementation, N=2, the reflectance of the calibration samples are known, and the expression in Eq 2 is minimized with respect to F0(λ,r) and F1(λ,r) separately for each wavelength λ and position r.

In an alternative embodiment, parameters of one or more calibration samples, such as the thicknesses of films, are unknown. In this case, the following expression is minimized $$\sum_{\lambda}\sum_{n=1}^{N}\left(\frac{S(n,1,\lambda,r)S(n,2,\lambda,r_0)}{S(n,2,\lambda,r)S(n,1,\lambda,r_0)} - F0(\lambda,r) - F1(\lambda,r)R_c(n,\lambda,r)\right)^2. \quad \text{Eq 3}$$

with respect to the unknown parameters of the calibration samples and F0(λ,r) and F1(λ,r) for all wavelengths simultaneously. The minimization is repeated for each position r.

In alternative embodiments, Eq 2 may include terms with additional calibration functions multiplied by powers of $R_c$. Eqs 1 and 2 thus apply to the linear, or first order calibration, and higher order calibrations are possible. In yet alternative embodiments, the reference reflector and measurements associated with it may be left out. In such cases, movable mirror 204 serves as the reference reflector. Alternative version of Eqs. 1 and 2 would yield measured reflectivity and calibration functions.

As seen above, reflectance is generally related to the ratio between the sample and monitor signals. Because both sample measurement signal and monitor signal come from light in the reflection path, in different states of the instrument 200, changes in this ratio are due to the reflectivity changes of the sample 116 and mirror 204 only, and not potential variations caused by utilizing different reflection paths and/or different detectors for the monitor and measurement signals. The reflection path is such that the light reflected off the mirror to the detector includes only elements which the light reflected from the sample to the detector will travel through. Thus, there are no elements in the reflection path from the mirror to the detector which are not included in the reflection path from the sample to the detector.

Figure 1:
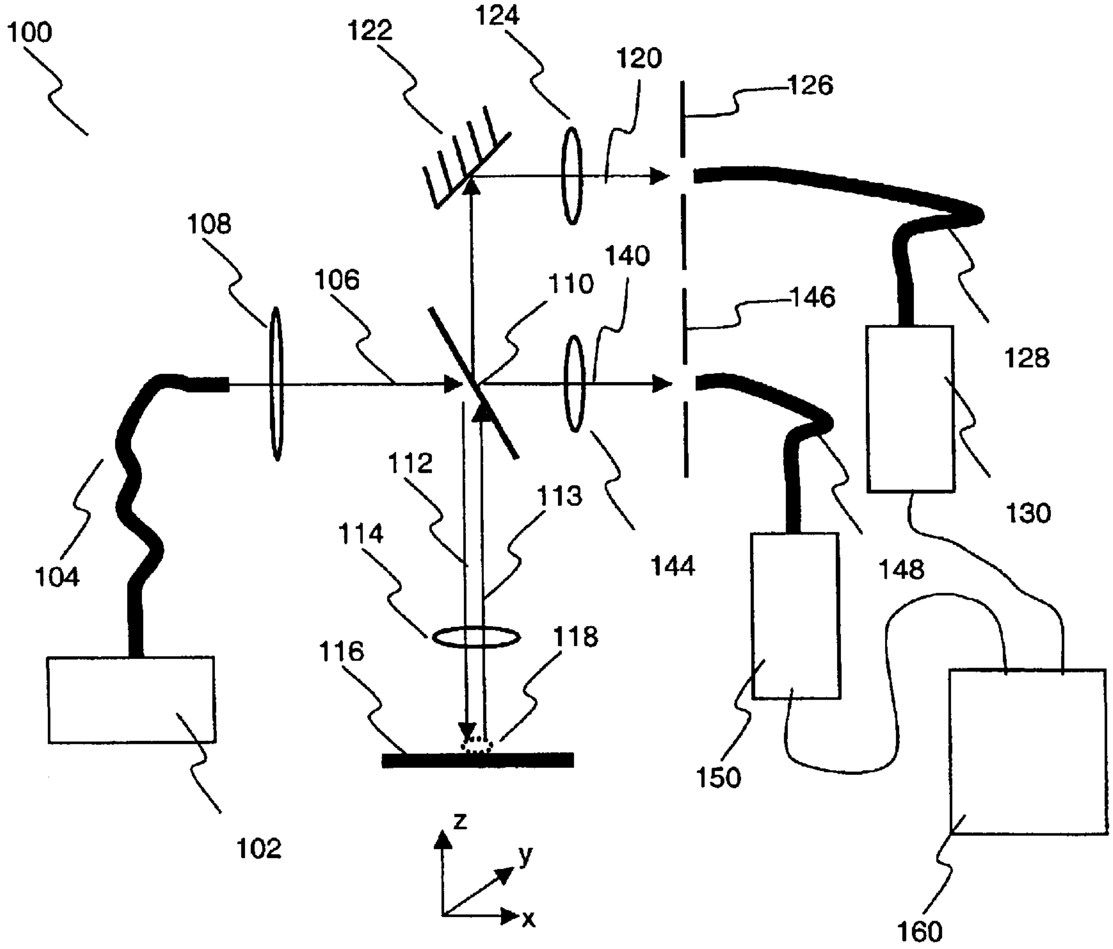
FIG. 1 is a schematic view illustrating a prior art spectrometer system.

Thus, in prior systems there is a much higher likelihood that the ratio between the monitor signal and the measurement signals depends not only on the reflectivity characteristics of the sample, which are presumed unknown, but also on the effects of the different reflection or transmission paths, and different characteristics of different detectors. For example, referring to FIG. 1, a spec of dust on lens 144 would affect the ratio measurement/monitor ratio. However, referring to FIGS. 2 and 3, a spec of dust on lens 224 will affect the measurement and monitor signals equally so that their ratio will remain constant. Similarly, different changes in temperature of detectors 130 and 150 in FIG. 1 are likely to change their efficiencies differently, and thus affect the measurement/monitor ratio. However, in the present invention there is only one detector, so the ratio will not change as long as the temperature and efficiency of the detector do not change over the short time required to sample the two signals. Thus, the present invention can provide for enhanced measurement accuracy of the reflection characteristics of the sample.

Figure 4:
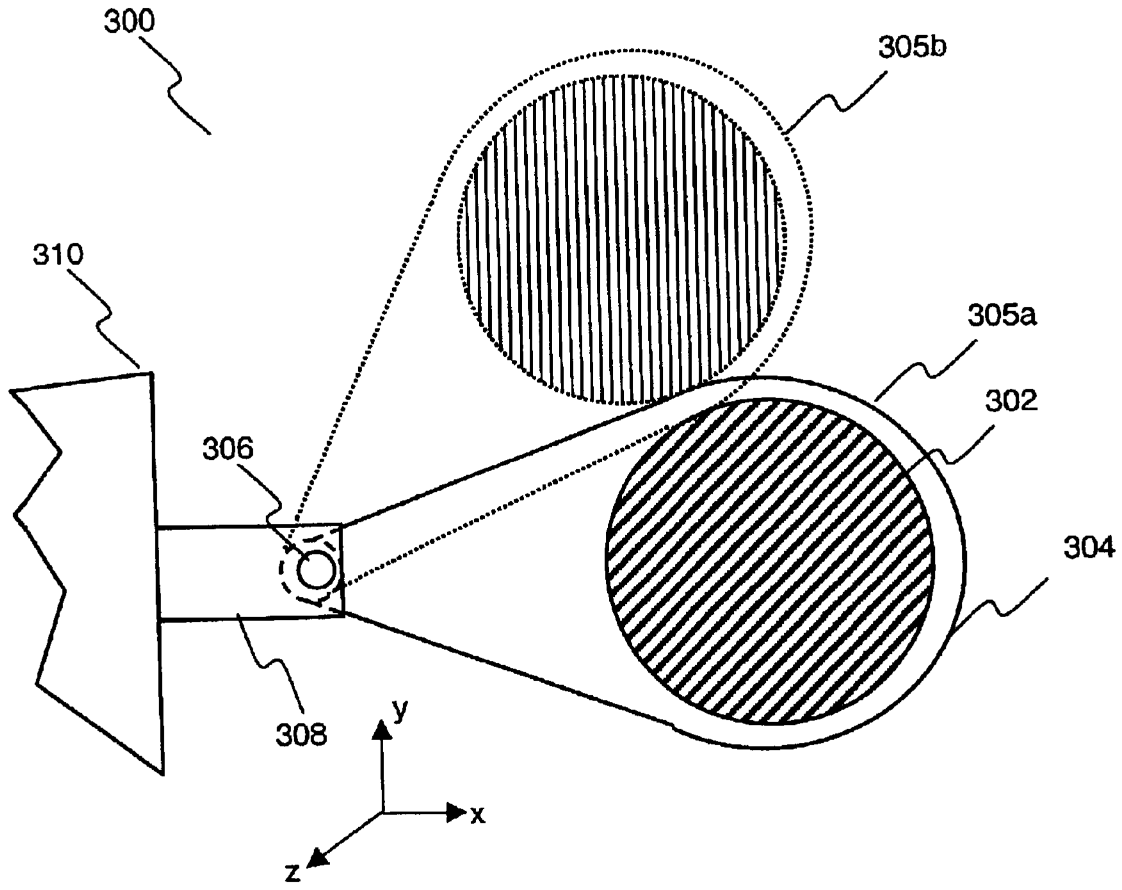
FIG. 4 is top view of an embodiment of a movable mirror and its mounting.
Figure 5:
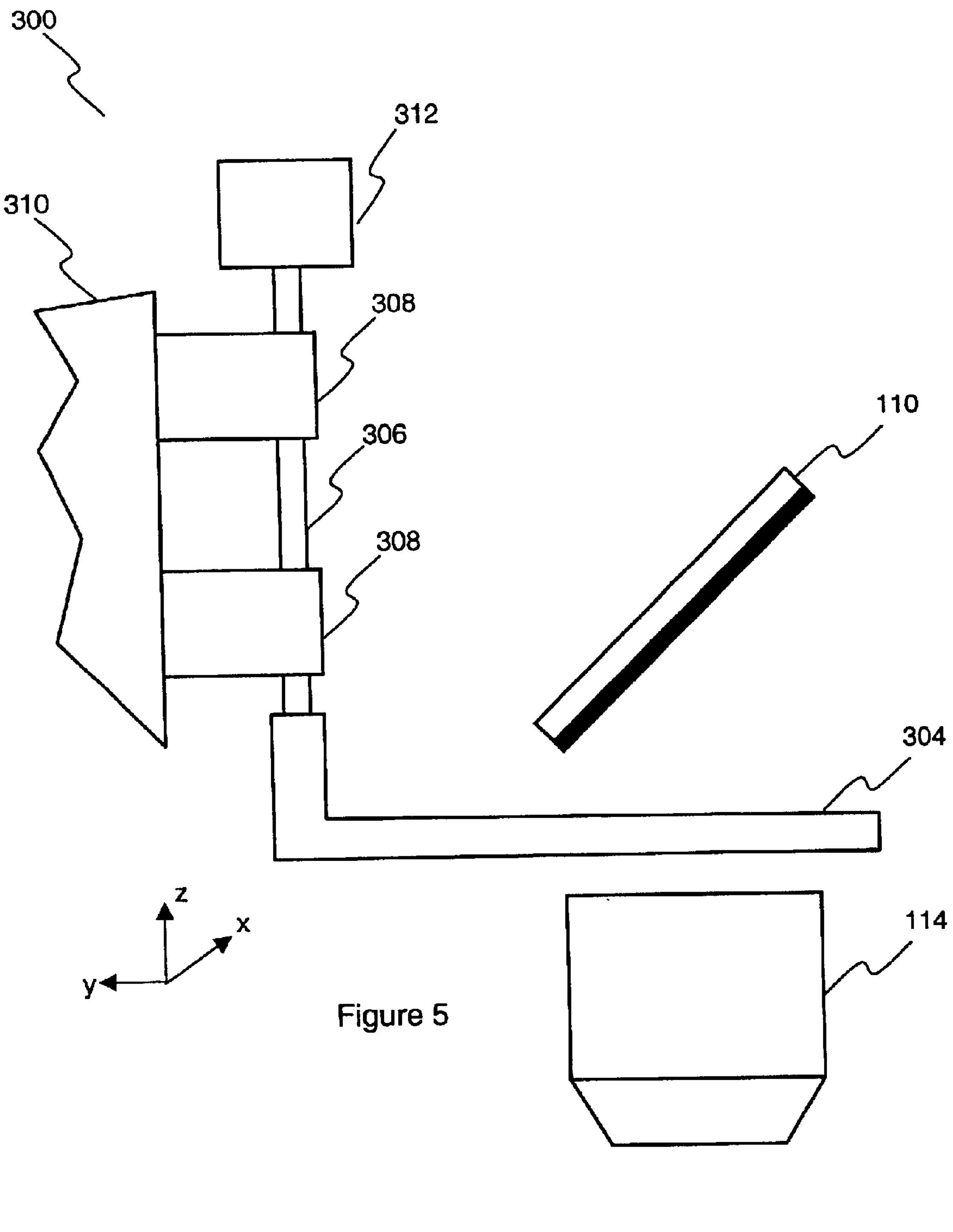
FIG. 5 is a side view of an embodiment of a movable mirror and components which enable its motion.

Movable mirror 204 may be implemented as shown in FIGS. 4 and 5. Viewed from above, as in FIG. 4, mirror 302 is held with bracket 304 which is allowed to rotate about axel 306 to positions 305*a* and 305*b* by bearings 308. Support 310 holds the bearings in a fixed relation to the rest of the optics in system 200, beam splitter 110, as shown in FIGS. 2, 3, and 5. Motor 312 turns axel 306, and consequently bracket 304. Motor 312 preferably has hard stops associated with locations 305*a* and 305*b*, to allow these positions to be highly reproducible. Two spaced bearings 308 are preferred to constrain motion of bracket 304 to be in a plane so that mirror 302 is always perpendicular to the optical axis of associated with path 206. Many alternative embodiments are possible. For example, mirror 302 may be allowed to rotate 360° C. about axel 306. Mirror 302 may rotate continuously, with the precise acquisitions times for measurement and monitor signals synchronized with the rotation. In yet alternative embodiments, both the sample and monitor signals may be sums of over alternating sample and monitor signal portions. This allows for, e.g., variations in lamp intensity at a faster rate.

While the present invention has been described in terms of the embodiments discussed above, those skilled in the art will recognize that the present invention may be practiced with modification to the above described embodiment and still be and within the spirit and scope of the appended claims. For example, one alternative embodiment could provide for positioning the movable mirror between the objective lens and the sample. Thus, the specifications and figures herein are to be regarded in an illustrative rather than a restrictive sense. Further, even though only certain embodiments have been described in detail, those having ordinary skill in the art will certainly understand that many other modifications are possible without departing from the teachings herein. All such modifications are intended to be encompassed within the following claims.

What is claimed is:

1. A system for measuring characteristics of a sample, including:

a light source for generating a beam of light which is directed toward a sample;

a mirror which can be moved between a first position and a second position, wherein in the first position the mirror is positioned between the light source and the sample such that light generated by the light source is reflected off the mirror and transmitted through a first path, wherein the first path consists of a reflection path, wherein in the second position the mirror is positioned such that it is not between the light source and the sample, and light generated by the light source is reflected off the sample and transmitted through the reflection path;

a detector coupled to the reflection path which generates a monitor signal in response to receiving light reflected from the mirror, and generates a measurement signal in response to light reflected from the sample; and a beam splitter positioned between the light source and the sample, wherein light from the light source is incident on the beam splitter and directed from the beam splitter toward the sample.

2. The system of claim 1 further including an objective lens positioned between the beam splitter and the sample.

3. The system of claim 1, wherein in the first position the mirror is positioned between the beam splitter and the sample.

4. The system of claim 1 further including a processor coupled to the detector, wherein the processor receives the monitor signal form the detector, and receives the measurement signal from the detector, and determines the characteristics of the sample based on the ration of the measurement signal relative to the monitor signal.

5. A system for measuring characteristics of a sample, including:

a light source for generating a beam of light which is directed toward a sample;

a mirror which can be moved between a first position and a second position, wherein in the first position the mirror is positioned between the light source and the sample such that light generated by the light source is reflected off the mirror and transmitted through a first path, wherein the first path consists of a reflection path, wherein in the second position the mirror is positioned such that it is not between the light source and the sample, and light generated by the light source is reflected off the sample and transmitted through the reflection path; and a detector coupled to the reflection path which generates a monitor signal in response to receiving light reflected from the mirror, and generates a measurement signal in response to light reflected from the sample;

wherein the reflection path includes:

an optic fiber;

a beam splitter;

and wherein the detector is coupled to the optic fiber.

6. The system of claim 5 further including a processor coupled to the detector, wherein the processor receives the monitor signal from the detector, and receives the measurements signal from the detector, and determines the characteristics of the sample based on the ratio of the measurement signal relative to the monitor signal.

7. A system for measuring characteristics of a sample, including:

a light source for generating a beam of light which is directed toward a sample;

a mirror which can be moved between a first position and a second position, wherein in the first position the mirror is positioned between the light source and the sample such that light generated by the light source is reflected off the mirror and transmitted through a first path, wherein the first path consists of a reflection path, wherein in the second position the mirror is positioned such that it is not between the light source and the sample, and light generated by the light source is reflected off the sample and transmitted through the reflection path; and a detector coupled to the reflection path which generates a monitor signal in response to receiving light reflected from the mirror, and generates a measurement signal in response to light reflected from the sample;

wherein the detector is a spectrometer which generates signals corresponding to intensity of the light at different wavelengths.

8. The system of claim 7 further including a processor coupled to the detector, wherein the processor receives the monitor signal from the detector, and receives the measurement signal from the detector, and determines the characteristics of the sample based on the ratio of the measurements signal relative to the monitor signal.

9. The system of claim 7 further including a beam splitter positioned between the light source and the sample, wherein light from the light source is incident on the beam splitter and directed from the beam splitter toward the sample.

10. A system for measuring characteristics of a sample, including:

a light source for generating a beam of light which is directed toward a sample;

a mirror which can be moved between a first position and a second position, wherein in the first position the mirror is positioned between the light source and the sample such that light generated by the light source is reflected off the mirror and transmitted through a first path, wherein the first path consists of a reflection path, wherein in the second position the mirror is positioned such that it is not between the light source and the sample, and light generated by the light source is reflected off the sample and transmitted through the reflection path; and a detector coupled to the reflection path which generates a monitor signal in response to receiving light reflected from the mirror, and generates a measurement signal in response to light reflected from the sample;

wherein the reflection path includes:

an optic fiber, and the detector is coupled to the optic fiber.

11. The system of claim 10 further including a processor coupled to the detector, wherein the processor receives the monitor signal from the detector, and receives the measurement signal from the detector, and determines the characteristics of the sample base on the ratio of the measurement signal relative to the monitor signal.

12. An optical system for measuring characteristics of samples, including:

a light source for generating a beam of light;

a beam splitter for directing the beam of light toward a sample;

a lens disposed between the beam splitter and the sample for focusing the beam of light on the sample, such that a measurement beam of light is reflected off the sample, wherein after the measurement beam is reflected off the sample, it is transmitted through a reflection path;

a detector positioned to receive light transmitted through the reflection path wherein in response to receiving light transmitted through the reflection path the detector generates a signal corresponding to the light transmitted through the reflection path;

a mirror which can be moved between a first position and a second position, wherein in the first position the mirror is positioned between the beam splitter and the sample, such that light directed by the beam splitter toward the sample is incident upon the mirror and reflected through a first path, wherein the first path consists of the reflection path, wherein in the second position the mirror is positioned such that light directed by the beam splitter toward the sample is reflected off the sample along the reflection path; and a processor coupled to the detector which uses a first signal generated by the detector in response to receiving light reflected from the mirror and a second signal generated by the detector in response to light reflected from the sample, to determine characteristics of the sample.

* * * * *